United States Patent
DeVries et al.

(10) Patent No.: US 11,647,899 B2
(45) Date of Patent: May 16, 2023

(54) DEVICES, SYSTEMS AND METHODS FOR ACCESSING A BODY LUMEN

(71) Applicant: Boston Scientific Scimed, Inc., Maple Grove, MN (US)

(72) Inventors: Robert B. DeVries, Northborough, MA (US); Peter L. Dayton, Brookline, MA (US); Ryan Hartman, Kingston, MA (US); Douglas Melanson, Natick, MA (US); Barry Weitzner, Acton, MA (US); Evan Wilder, Boston, MA (US); Chris Davis, Grafton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 854 days.

(21) Appl. No.: 16/440,017

(22) Filed: Jun. 13, 2019

(65) Prior Publication Data

US 2019/0380565 A1    Dec. 19, 2019

Related U.S. Application Data

(60) Provisional application No. 62/684,981, filed on Jun. 14, 2018.

(51) Int. Cl.
| | | |
|---|---|---|
| *A61B 1/015* | (2006.01) | |
| *A61B 1/018* | (2006.01) | |
| *A61M 25/09* | (2006.01) | |
| *A61M 25/01* | (2006.01) | |

(Continued)

(52) U.S. Cl.
CPC .............. *A61B 1/015* (2013.01); *A61B 1/018* (2013.01); *A61M 25/09* (2013.01); *A61B 1/0057* (2013.01);

(Continued)

(58) Field of Classification Search
CPC ................................................ A61B 2018/144
See application file for complete search history.

(56) References Cited

U.S. PATENT DOCUMENTS 5,547,469 A * 8/1996 Rowland ................ A61B 18/10
                                                       606/159
5,599,299 A * 2/1997 Weaver ............. A61M 25/0026
                                                       600/585

(Continued)

FOREIGN PATENT DOCUMENTS

GB            2255281 A   * 11/1992     ............. A61B 1/042

*Primary Examiner* — John P Leubecker
(74) *Attorney, Agent, or Firm* — Seager, Tufte & Wickhem, LLP

(57) ABSTRACT

The present disclosure relates to medical devices that that include the following: a flexible elongate tube having a proximal end and a distal end configured to be directed toward an opening of a body lumen; a first lumen extending from the distal end of the tube proximally along the tube and having a fluid connection for a fluid source at its proximal end; a second lumen extending from the distal end of the tube proximally along the tube, the second lumen configured to accept a guidewire extending along the second lumen; and a wire filament extending along the elongate tube, a distal end of the filament connected to the distal end of the elongate tube, a proximal portion of the wire extending at least partially along the elongate tube, and a distal portion of the wire extending external to the elongate tube.

17 Claims, 7 Drawing Sheets

(51) Int. Cl.
　　　*A61M 25/00*　　(2006.01)
　　　*A61M 31/00*　　(2006.01)
　　　*A61B 1/005*　　(2006.01)

(52) U.S. Cl.
　　　CPC ..... *A61M 25/0032* (2013.01); *A61M 25/0122* (2013.01); *A61M 25/0133* (2013.01); *A61M 31/005* (2013.01); *A61M 2025/004* (2013.01); *A61M 2025/0037* (2013.01); *A61M 2025/0177* (2013.01)

(56) References Cited

U.S. PATENT DOCUMENTS

| | | | | |
|---|---|---|---|---|
| 5,628,746 | A * | 5/1997 | Clayman | A61B 18/08 606/45 |
| 8,560,053 | B2 | 10/2013 | Pasricha | |
| 2003/0114877 | A1 * | 6/2003 | Gellman | A61M 25/10 606/192 |
| 2007/0265617 | A1 * | 11/2007 | Falkenstein | A61B 18/1492 606/48 |
| 2010/0256448 | A1 * | 10/2010 | Smith | A61B 1/0055 600/156 |
| 2013/0023854 | A1 * | 1/2013 | Reydel | A61M 25/003 604/528 |
| 2014/0088567 | A1 * | 3/2014 | Nieman | A61M 1/85 604/533 |
| 2014/0358089 | A1 * | 12/2014 | Kappel | A61B 1/00094 604/176 |
| 2015/0011834 | A1 * | 1/2015 | Ayala | A61B 17/0218 29/428 |
| 2016/0256217 | A1 * | 9/2016 | Hutchins | A61B 18/1492 |
| 2016/0331452 | A1 * | 11/2016 | Oguni | A61B 1/018 |
| 2019/0008364 | A1 * | 1/2019 | Yamanaka | A61M 25/01 |
| 2020/0375656 | A1 * | 12/2020 | Kachaamy | A61M 25/09 |

* cited by examiner

US 11,647,899 B2

DEVICES, SYSTEMS AND METHODS FOR ACCESSING A BODY LUMEN

PRIORITY

This application claims the benefit of priority under 35 USC § 119 to U.S. Provisional Patent Application Ser. No. 62/684,981, filed Jun. 14, 2018, which is incorporated by reference herein in its entirety and for all purposes.

FIELD

The present disclosure relates generally to the field of medical devices and establishing access to body lumens. In particular, the present disclosure relates to medical devices, systems and methods for facilitating access to an opening of a body lumen through an endoscope by at least partially dilating the opening with fluid from a fluid source prior to contacting the body lumen.

BACKGROUND

Medical professionals sometimes face significant technical challenges when accessing a body lumen; for example, when performing endoscopic cannulation procedures that may require advancing a guidewire and/or endoscopic accessory tool (e.g., sphincterotome, cannula, catheter, or the like) against, into, or through challenging patient anatomies. For example, a target body lumen may be oriented at a difficult angle relative to the endoscopic accessory tool, have a very small or sealed opening, or include a tortuous anatomy, blockages (e.g., stones, or the like), or benign or malignant structures. To facilitate smooth and efficient entry of a guidewire and endoscopic accessory tool into/through a target body passageway, medical professionals may manually rotate, oscillate, linearly advance, and/or reciprocate the endoscopic accessory tool, and by proxy the guidewire itself, to "wiggle" the guidewire and endoscopic accessory tool against, into, or through the body lumen with frictional forces exerted against the opening or tissue wall of the body lumen. Precise control of the force of movement imparted to the accessory tool and guidewire largely remains crude and uncontrolled. Even experienced medical professionals often require multiple attempts to achieve successful opening or entering of body lumens, especially when working against the natural friction and abnormal patient-specific pathologies of the specific body lumen. Naturally, the likelihood of causing trauma to the tissues comprising or surrounding the target body passageway increases with the number of opening or entry attempts. In some instances, the medical professional may be required to abort the procedure entirely. In other instances, the traumatized tissues may be prone to harmful and potentially life-threatening post-operative inflammation.

A variety of advantageous medical outcomes may be realized by the medical devices, systems, and methods of the present disclosure, which facilitate access to body lumens in challenging patient-specific anatomies.

SUMMARY

Embodiments of the present disclosure may assist generally with accessing of a body lumen without the need to touch, abrade, or compress the body lumen. In one embodiment, a device for accessing a body lumen according to the present disclosure includes a medical device that may have a flexible elongate tube that may have a proximal end and a distal end configured to be directed toward an opening of a body lumen. A first lumen may extend from the distal end of the tube at least partially along the tube toward the proximal end of the tube. The first lumen may have a fluid connection at a proximal end for a fluid source. A second lumen may extend from the distal end of the tube at least partially along the tube toward the proximal end of the tube. The second lumen may be configured to accept a guidewire extending along the second lumen. A wire filament may extend along the elongate tube. A distal end of the filament may be connected to the distal end of the elongate tube. A proximal portion of the wire may extend at least partially along the elongate tube. A distal portion of the wire may extend external to the elongate tube.

In various embodiments, a third lumen may extend along the tube and may be configured to deliver a contrast agent. A bifurcated lumen may be at the distal end of the tube. The bifurcated lumen may include a partition wall separating the bifurcated lumen into two half-lumens. The second lumen may transition to one of the two half-lumens. The third lumen may transition to the other of the two half-lumens. The first lumen may be configured to deliver a gas as the fluid source from the first lumen at the distal end of the tube to at least partially open the body lumen for access substantially without the medical device contacting the body lumen. A radial skirt may be about the elongate tube. The skirt may have a funnel shape tapering inward toward the distal end of the tube and may be in fluid communication with an opening to the first lumen. The skirt may have an outer diameter configured to be in substantial contact with an inner diameter of a working channel of an endoscope. A channel may extend at least partially along an outer surface of the elongate tube and may transition to the second lumen. A fourth lumen may extend along the tube and a handle at the proximal end of the tube and may be connected to the proximal end of the wire filament. The proximal portion of the wire may slidably extend within the fourth lumen. The handle may be configured to slide the wire filament within the fourth lumen such that the distal end of the tube may be directed toward the opening of the body lumen.

In another embodiment, a system may include an endoscope that may have a proximal end with an axial opening, a distal end with a radial opening and a working channel extending therebetween. The system may include a fluid source. The system may include a guidewire. A medical device may extend through the working channel. The medical device may be configured to be directed toward an opening of a body lumen. The medical device may include a flexible elongate tube having a proximal end and a distal end. A first lumen may extend from the proximal end of the tube to the distal end of the tube and may have a fluid connection at a proximal end for the fluid source.

In various embodiments, a first lumen may be configured to accept the guidewire through a first aperture at the proximal end of the first lumen, the guidewire extending along the first lumen. The first lumen may include a second aperture at the proximal end of the first lumen that is in fluid communication with the fluid source. A medical device may include a second lumen extending from the distal end of the tube at least partially along the tube toward the proximal end of the tube. The second lumen may be configured to accept the guidewire extending along the second lumen. The second lumen may extend from the distal end of the tube at least partially along the tube toward the proximal end of the tube. The second lumen may be configured to accept the guidewire extending along the second lumen. A wire filament may extend along the elongate tube. A distal end of the filament may be connected to the distal end of the elongate tube. A proximal portion of the wire may extend at least partially along the elongate tube. A distal portion of the wire may extend external to the elongate tube. The first lumen may be configured to deliver a gas as the fluid source from the first lumen at the distal end of the tube to at least partially open the body lumen for access by the guidewire without the medical device contacting the body lumen. A regulator may be in line with the first lumen and may be configured for regulating a flow of a fluid from the fluid source into the first lumen. A flow rate of fluid from the fluid source exiting the first lumen may be adjustable. The regulator may adjust the flow rate in the range of about 400 cubic centimeters per minute to about 800 cubic centimeters per minute. A supply tube may be in fluid communication with the fluid source and the first lumen. A filter may be in-line with the supply tube and may be configured to filter the fluid from the fluid source prior to entering the first lumen. A partition wall may be at least partially destructible at the distal end of the tube. The fluid source may be one of a tank, a house supply, or a disposable cartridge. The fluid source may comprise $CO_2$ gas. A nozzle may be at a distal end of the first lumen. The wire filament may be configured to be energized for cutting tissue of the body lumen. The handle may include an electrical connection for a radiofrequency energy source to energize the wire filament. The regulator may comprise a foot pedal. The fluid source may comprise a pharmacological agent.

In a further embodiment, a method of accessing a body lumen may include extending an endoscope having a working channel into a patient. An elongate tube that may have a distal end and a lumen may be extended through the working channel. The distal end of the tube may be directed toward an opening of the body lumen. A fluid may be flowed from a fluid source through the lumen of the tube to the distal end of the tube. The fluid may be delivered to the opening to at least partially dilate the opening of the body lumen with the fluid.

In various embodiments, a guidewire may be extended through the tube into the body lumen. The tube may be removed from about the guidewire and the working channel such that the guidewire is left within the working channel and the body lumen. Another tube may be inserted within the working channel over the guidewire and into the body lumen. A contrast agent may be delivered into the body lumen. Directing the distal end of the tube may include aligning the tube substantially axially with the opening of the body lumen. The distal end may be aligned at a distance of about 5 millimeters to about 10 millimeters away from the opening of the body lumen. A flow rate of the fluid flowing through the tube may be adjusted. The endoscope may be extended through the stomach and into the duodenum of the patient.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1A:
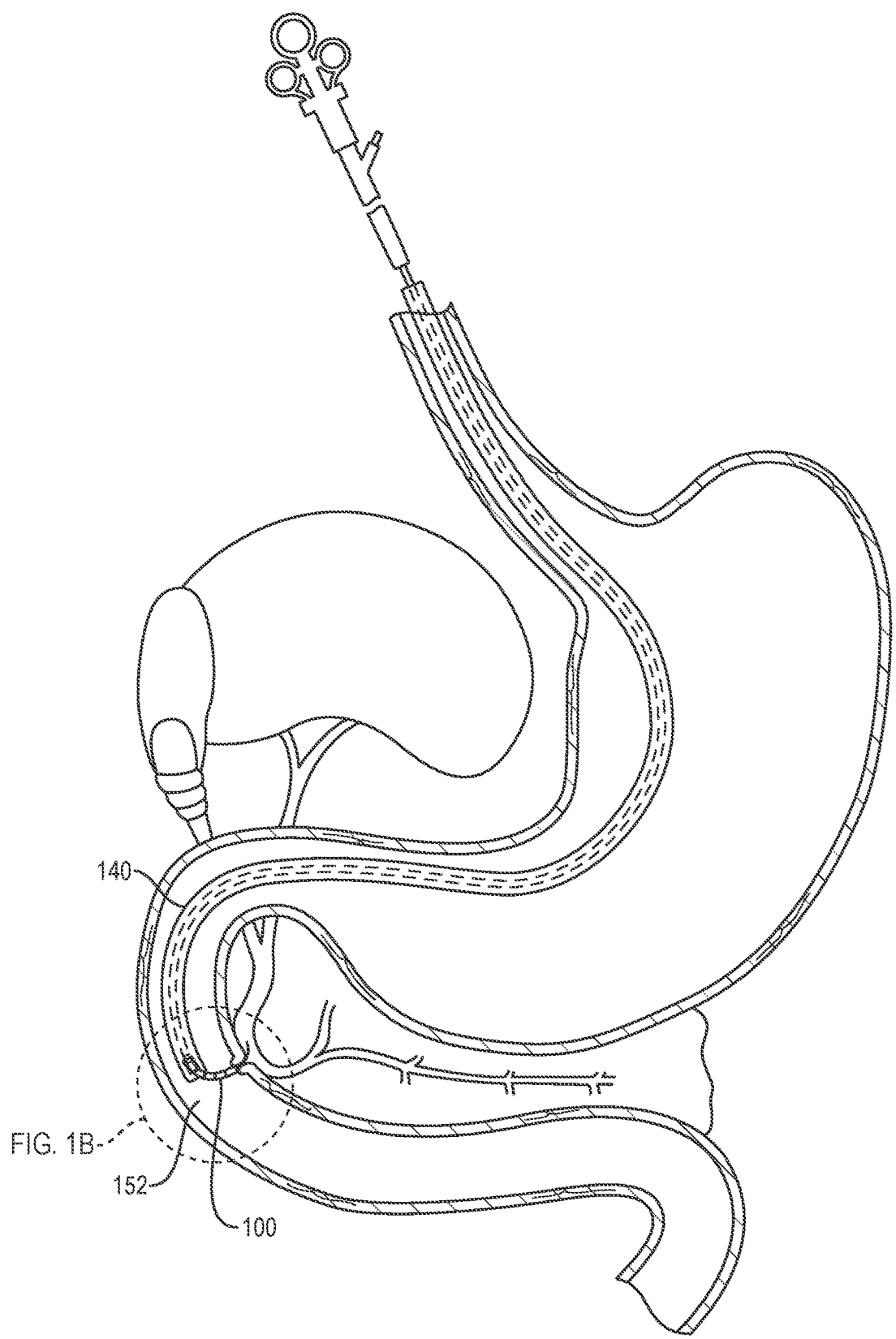
FIG. 1A illustrates a conventional endoscopic system and accessory device accessing the papilla of a patient through the stomach and the duodenum.

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to medical devices and systems (e.g., endoscopic devices, accessory tools, and/or guidewires inserted through a duodenoscope, near or through a papilla, or the like) for selective access to, aligning with, and/or cannulation of the common bile duct (CBD) or pancreatic duct (PD) during an Endoscopic Retrograde Cholangiopancreatography (ECRP) procedure, it should be appreciated that such medical devices and systems may be used in a variety of medical procedures which require navigating one or more accessory tools through ductal, luminal, vascular, or body lumen anatomies, including, for example, interventional radiology procedures, balloon angioplasty/angiography procedures, thrombolysis procedures, urological or gynecological procedures, and the like. The disclosed medical devices and systems may be inserted via different access points and approaches, e.g., percutaneously, endoscopically, laparoscopically, or some combination thereof.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional when introducing a medical device into a patient, while the term "proximal" refers to the end closest to the medical professional when introducing a medical device into a patient.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Figure 1B:
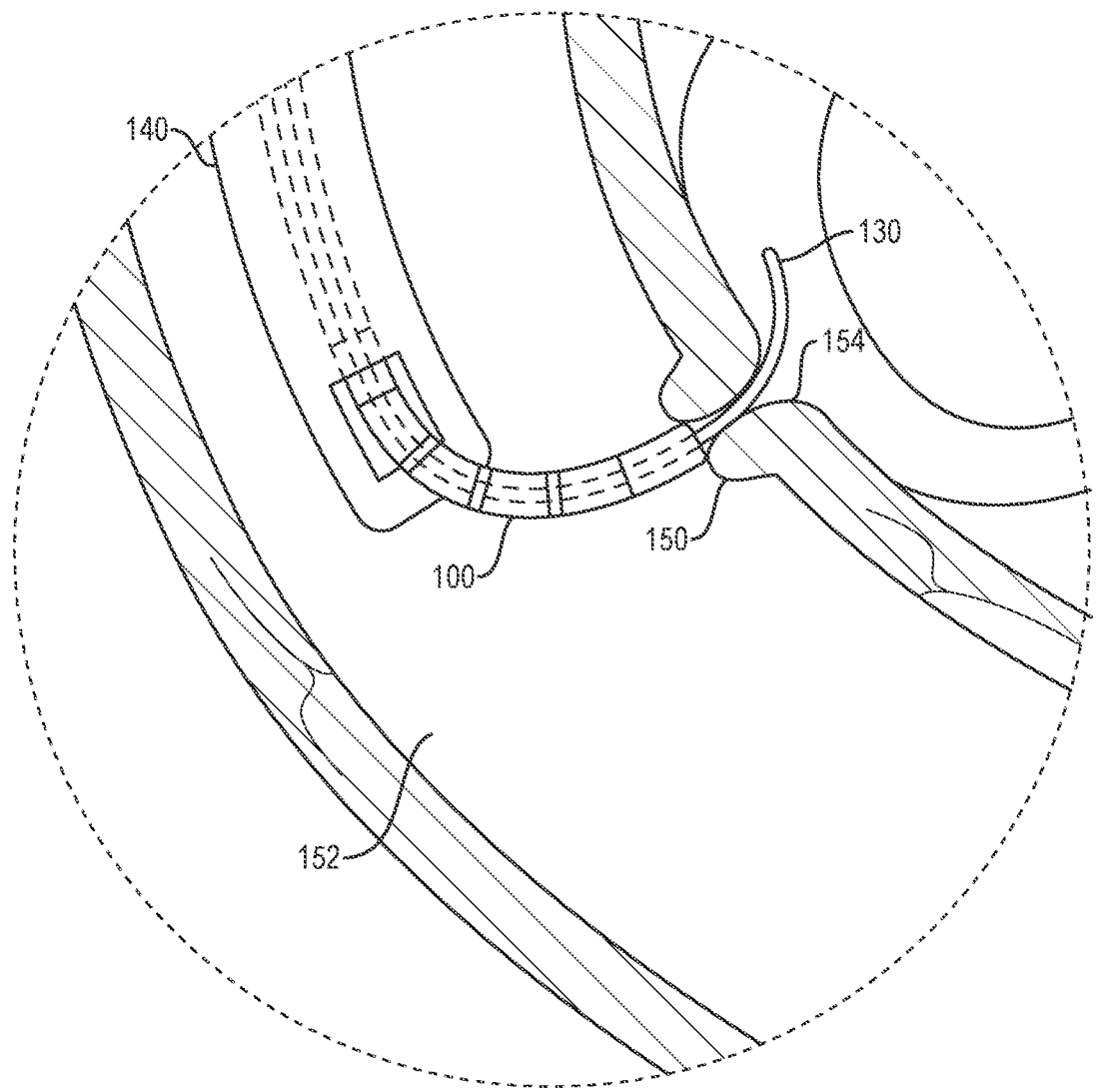
FIG. 1B illustrates a closer view of the papilla and surrounding system and tissue of FIG. 1A.

With reference to FIGS. 1A and 1B, a known process of selective cannulation during an ERCP procedure is illustrated, which shows a guidewire 130 and/or an endoscopic accessory device 100 being passed towards, against, and/or through a body lumen such as the major papilla 150 (e.g., ampullary entry) near the descending duodenum 152 to access the Sphincter of Oddi Complex 154. A distal portion of a medical device 140 (e.g., duodenoscope) may be positioned within the descending duodenum 152. The guidewire 130 and the medical device 100 may be advanced through a working channel of the duodenoscope 140 towards the major papilla 150. Additionally, the guidewire 130 and/or the medical device 100 may be advanced against or through the major papilla 150. Accessing the papilla 150 may be difficult because the opening is small compared to many medical devices, the opening may be completely collapsed/closed, and/or the opening may extend into the descending duodenum 152 at an angle that may be difficult to visualize and/or access. Thus, a medical professional may be required to manipulate the medical device 100 and guidewire 130 by manually rotating the duodenoscope 140 and/or using an elevator within the distal end of the duodenoscope 140 in an attempt to better align or orient the device 100 and/or guidewire 130 with respect to the duodenoscope and the opening of the papilla. Difficult cannulation procedures in which the medical professional fails to access the Sphincter Papillae within a certain time limit, or after a certain number of unsuccessful attempts, as mentioned above, may lead to significant post-procedure complications, such as post-ECRP pancreatitis (PEP).

With conventional techniques, a medical professional accessing a body lumen (e.g., a duct, such as a papilla, or the like) by manipulating a medical device against or into the opening of the body lumen may subject the walls of the opening of the body lumen to compressive forces. Compression of a body lumen opening or the body lumen itself can cause buckling in what may be described as the "accordion effect". Should a medical device be inserted into a body lumen without the accordion effect, opening and/or maintaining patency of the body lumen through repeated inserting of the medical device and/or a guidewire or other instruments may cause undue irritation to the body tissue from friction.

Accessing a body lumen substantially without or without contact from a medical device and allowing insertion of the guidewire directly into the lumen substantially without or without contacting the body lumen opening may decrease both tissue abrasion and lumen compression when compared to known medical devices and techniques. In various embodiments, the present disclosure relates to medical devices, systems and methods for selective cannulation of an opening to a body lumen, such as the CBD or PD, to treat a variety of indications, such as hepatobiliary indications during an ECRP procedure. Atraumatic contact and/or entry of a guidewire and/or an endoscopic accessory tool with or into the luminal structures of the hepatobiliary system may be achieved through controlled reduction or elimination of friction by using fluid at the distal end of the access device to move or open the lumen and/or surrounding tissue substantially without or without device contact.

Figure 2A:
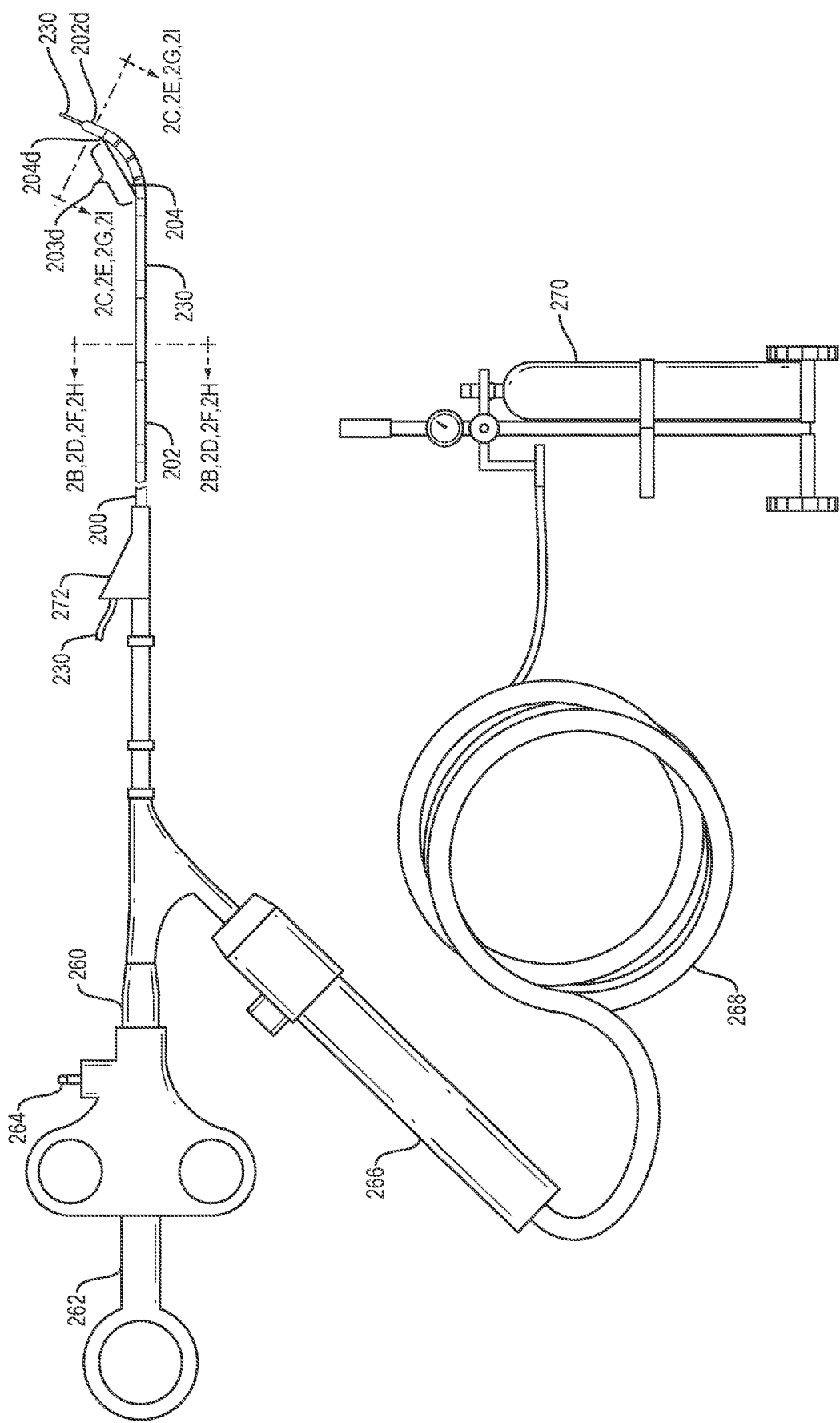
FIG. 2A illustrates an exemplary device and system for accessing a body lumen, according to an embodiment of the present disclosure.

With reference to FIG. 2A, an embodiment of a system according to the present disclosure is illustrated, which includes a medical device 200 with a flexible elongate tube 202. The tube 202 has a proximal end and a distal end $202_d$. The distal end $202_d$ is configured to be directed toward an opening of a body lumen. The proximal end of the tube 202 is connected to a handle 260. A wire filament 204 extends along the elongate tube 202 and may be energized for the purpose of cutting tissue within a patient. The wire filament 204 has a proximal end connected to a manipulating and/or actuating portion 262 of the handle 260, and a proximal portion extending at least partially within the tube 202. The wire filament 204 also has a distal portion $203_d$ extending external to the elongate tube 202, and a distal end $204_d$ of the filament 204 connected to the distal end $202_d$ of the elongate tube 202. The wire filament 204 may be received within a lumen of the tube 202, e.g., a fourth lumen of the tube 202 as described below, at least along a proximal portion of the filament 204, and configured to slide within the lumen. The manipulating portion 262 of the handle 260 may be manipulated to slide the wire filament 204. Sliding the wire filament 204 may also move the distal end $202_d$ of the elongate tube 202. Therefore, the manipulating portion 262 of the handle 260 may be manipulated to move the distal end $202_d$ of the elongate tube 202, for example, to direct the distal end $202_d$ toward the opening of a body lumen. The handle 260 includes an electrical connection 264 for an energy source (e.g., a radiofrequency energy source, or the like) to energize the wire filament 204. A first lumen extends from the proximal end of the tube 202 to the distal end $202_d$ of the tube 202. The first lumen has a fluid connection at a proximal end for a pressurized fluid source 270 (e.g., a $CO_2$ tank). The first lumen at the distal end $202_d$ of the tube 202 moves along with the distal end $202_d$ (e.g., toward an opening of a body lumen). The first lumen is configured to apply a fluid (e.g., a gas) from the fluid source to open or partially open the body lumen for access by the guidewire 230 and/or the elongate tube 202 substantially without or without the elongate tube 202 contacting the body lumen. Once opened or partially opened, the wire filament may be energized to further enlarge the opening. A filter 268 (e.g., a 0.1 micro filter) is in fluid communication with the first lumen distal to or downstream of the fluid source 270 and proximal to or upstream of the first lumen. A flow regulator 266 in fluid communication with the first lumen may be used to regulate the flow of fluid from the fluid source within the first lumen. The flow regulator 266 may include a valve configured to allow a user to vary the flow rate of the fluid through the device 200. In some embodiments, the flow regulator may be an on/off valve. The valve may be, e.g., a trumpet valve. A relief hole and/or valve may be located along the fluid path to release pressure from the system if the pressure of the fluid becomes too high for the procedure or for the patient's safety due to, e.g., a blockage in a lumen or perhaps a failure of the regulator. The relief hole may include a one-way valve that opens at a certain threshold of pressure. Fluid from the fluid source 270 may be fed through the regulator to reduce the fluid pressure before the pressure relief hole or valve. The pressure of the fluid source 270 may be higher than a pressure of the fluid of the device 200. The regulator and/or the relief valve may protect the patient and device 200 from the higher pressure of the fluid source by down-regulating the pressure at the regulator or providing a relief threshold at the relief hole or valve if pressure exceeds the threshold. If the regulator fails or is set incorrectly, the pressure relief valve may open to prevent an undesirably high pressure and/or high volume of fluid from entering the device 200. A range of suitable fluid pressure for the system or device delivered from the downstream side of the regulator and/or the relief valve may be, e.g. about 10 psi to about 30 psi. The guidewire 230 may be used to guide the medical device 200 or other instruments to a target area in the body lumen once the opening of the body lumen has been accessed. The guidewire 230 may extend out of aperture port 272. The aperture port 272 may be located at the distal end of the handle 260. The aperture port and tube may be configured so that the guidewire 230 may be stripped through the side of the tube 202 for a rapid removal or exchange of devices. The medical device 200 or other instruments may be navigated over the guidewire 230, e.g., near or through the body lumen. The elongate tube 202 has a second lumen that is configured to accept a guidewire 230. The second lumen extends from the distal end $202_d$ of the tube 202 at least partially along the tube 202 toward the proximal end of the tube 202. The elongate tube 202 may include a third lumen configured to be in fluid communication with a source of a contrast agent and to deliver the contrast agent to the body lumen and associated tissue. The contrast agent may be supplied to the third lumen via a syringe attached to a luer connector on the handle 260, for example. The contrast agent may be delivered into the body lumen and may be used to temporarily improve imaging of the inside of the body lumen such as, e.g., by x-ray, computed tomography (CT), or magnetic resonance (MR) imaging, ultrasound, and the like.

Figure 2B:
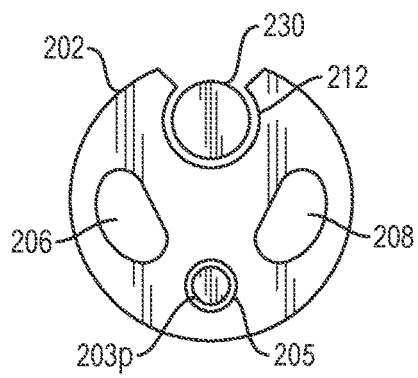
FIGS. 2B and 2C illustrate exemplary cross-sections of the device of FIG. 2A at the portions called out as "2B-2B" and "2C-2C", respectively, according to an embodiment of the present disclosure.
Figure 2C:
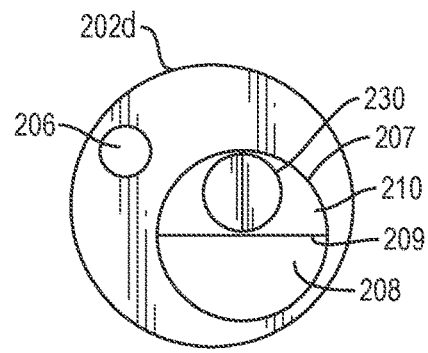

With reference to FIGS. 2B through 2C, an embodiment of a system according to the present disclosure is illustrated, which includes a cross-section of a device, such as device 200 of FIG. 2A, that varies between 2B-2B and 2C-2C. An embodiment of a device may have the cross-section of FIG. 2B at cross-section 2B-2B and the cross-section of FIG. 2C at cross-section 2C-2C. In this embodiment, a first lumen 206 extends along the elongate tube 202 at 2B-2B and has a fluid connection to a fluid source, such as the fluid source 270 of FIG. 2A. The first lumen 206 extends through the distal end $202_d$ of the elongate tube 202 at cross-section 2C-2C. A C-shaped channel 212 extending along the elongate tube 202 at cross-section 2B-2B removably holds the guidewire 230. A third lumen 208 at 2B-2B is configured to be in fluid communication with a source of a contrast agent and deliver the contrast agent. The C-channel 212 and third lumen 208 transition into a bifurcated lumen 207 at cross-section 2C-2C at the distal end $202_d$ of the tube 202. Bifurcated lumen 207 includes a partition wall 209 along at least a portion of the length of the bifurcated lumen 207 that separates the bifurcated lumen 207 into two half lumens; e.g., the third lumen 208 transitions into one of the half lumens in fluid communication with the source of contrast agent and a second lumen 210 transitions into the other of the two half lumens and is configured to accept the guidewire 230. The proximal portion $203_p$ of the wire filament 204 extends along the elongate tube 202 within, e.g., a fourth lumen 205 at 2B-2B. The wire filament 204 terminates proximal to the distal end $202_d$ of the elongate tube 202 prior to 2C-2C. The proximal portion $203_p$ of the wire filament 204 slidably extends within the fourth lumen 205, such that the distal end $202_d$ of the tube 202 may be directed toward the opening of the body lumen.

Figure 2D:
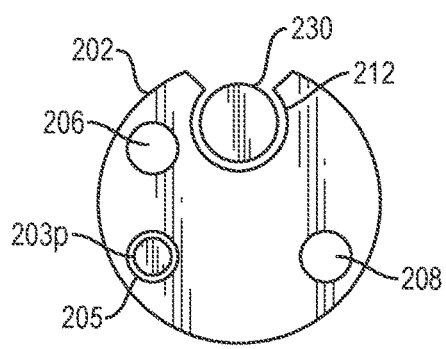
FIGS. 2D and 2E illustrate exemplary cross-sections of the device of FIG. 2A at the portions called out as "2D-2D" and "2E-2E", respectively, according to an embodiment of the present disclosure.
Figure 2E:
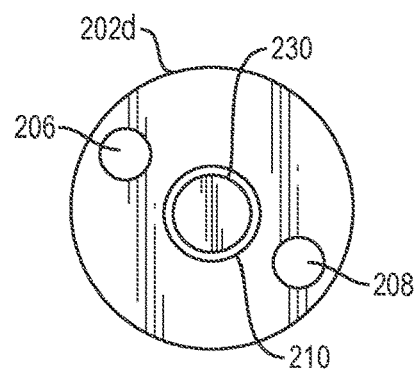

Alternatively, an embodiment of a medical device, such as the medical device 200 of FIG. 2A, may include a cross-section at 2D-2D as illustrated in FIG. 2D and a cross-section at 2E-2E as illustrated in FIG. 2E. The first lumen 206, which, e.g., is in fluid communication with the fluid source 270, extends through the elongate tube 202 at 2D-2D and through the distal end $202_d$ at 2E-2E. The C-shaped channel 212 extends along the elongate tube 202 at 2D-2D and removably holds the guidewire 230. The C-shaped channel 212 is in communication with and transitions to a second lumen 210 at 2E-2E. The guidewire 230 extends from the C-shaped channel 212 through the second lumen 210. The third lumen 208, which, e.g., is in fluid communication with a contrast agent source and is configured to deliver the contrast agent extends along the elongate tube 202 at 2D-2D and extends through the distal end $202_d$ at 2E-2E. The proximal portion $203_p$ of the wire filament 204 extends along the fourth lumen 205, which extends along the elongate tube 202 at 2D-2D. The distal end $204_d$ of the wire filament 204 terminates proximal to the distal end $202_d$ of the elongate tube 202 prior to cross-section 2E-2E.

Figure 2F:
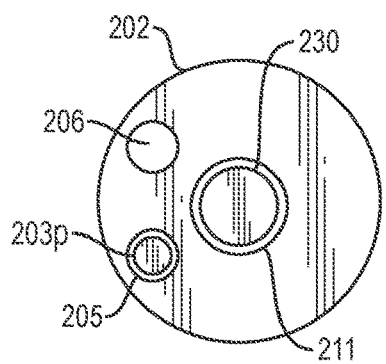
FIGS. 2F and 2G illustrate exemplary cross-sections of the device of FIG. 2A at the portions called out as "2F-2F" and "2G-2G", respectively, according to an embodiment of the present disclosure.
Figure 2G:
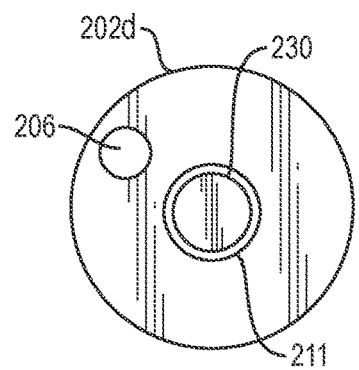

Alternatively, an embodiment of a medical device, such as the medical device 200 of FIG. 2A, may include a cross-section at 2F-2F as illustrated in FIG. 2F and a cross-section at 2G-2G as illustrated in FIG. 2G. The first lumen 206, which, e.g., is in fluid communication with the fluid source 270, extends through the elongate tube 202 at 2F-2F and through the distal end $202_d$ at 2G-2G. The second lumen 211 extends along the elongate tube 202 at 2F-2F and through the distal end $202_d$ of the elongate tube 202 at 2G-2G. The second lumen 211, e.g., is in fluid communication with a contrast agent source. The guide wire 230 also extends through the second lumen 211. The proximal portion $203_p$ of the wire filament 204 extends along a fourth lumen 205, which extends along the elongate tube 202 at 2F-2F. The distal end $204_d$ of the wire filament 204 terminates proximal to the distal end $202_d$ of the elongate tube 202 at 2G-2G.

Figure 2H:
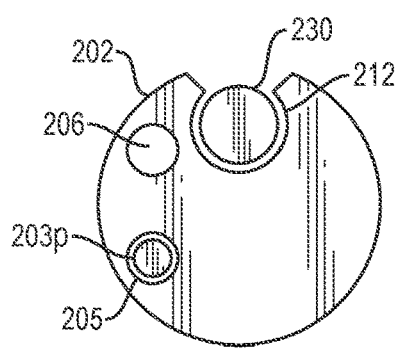
FIGS. 2H and 2I illustrate exemplary cross-sections of the device of FIG. 2A at the portions called out as "2H-2H" and "2I-2I", respectively, according to an embodiment of the present disclosure.
Figure 2I:
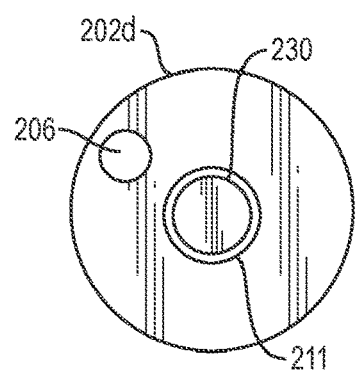

Alternatively, an embodiment of a medical device, such as the medical device 200 of FIG. 2A, may include a cross-section at 2H-2H as illustrated in FIG. 2H and a cross-section at 2I-2I as illustrated in FIG. 2I. The first lumen 206, which, e.g., is in fluid communication with the fluid source 270 and is also in fluid communication with a contrast agent source, extends through the elongate tube 202 at 2H-2H and through the distal end $202_d$ at 2I-2I. The C-shaped channel 212 extends along the elongate tube 202 at 2H-2H and removably holds the guidewire 230. The C-shaped channel 212 is in communication with and transitions to a second lumen 210 at 2I-2I. The guidewire 230 extends from the C-shaped channel 212 through the second lumen 210. The proximal portion $203_p$ of the wire filament 204 extends along a fourth lumen 205, which extends along the elongate tube 202 at 2H-2H. The distal end $204_d$ of the wire filament 204 terminates proximal to the distal end $202_d$ of the elongate tube 202 prior to cross-section 2I-2I.

In various embodiments, described here or otherwise within the scope of the present disclosure, the various lumens described above may be arranged in different configurations and combinations depending on the instrument and fluid requirements for a particular application. For example, a lumen configured for a guidewire may also be configured (or instead be configured) for a contrast agent, etc. Embodiments described and illustrated herein are not meant to exclusively include only those lumens, and do not necessarily need to include all of the lumens illustrated.

Figure 3:
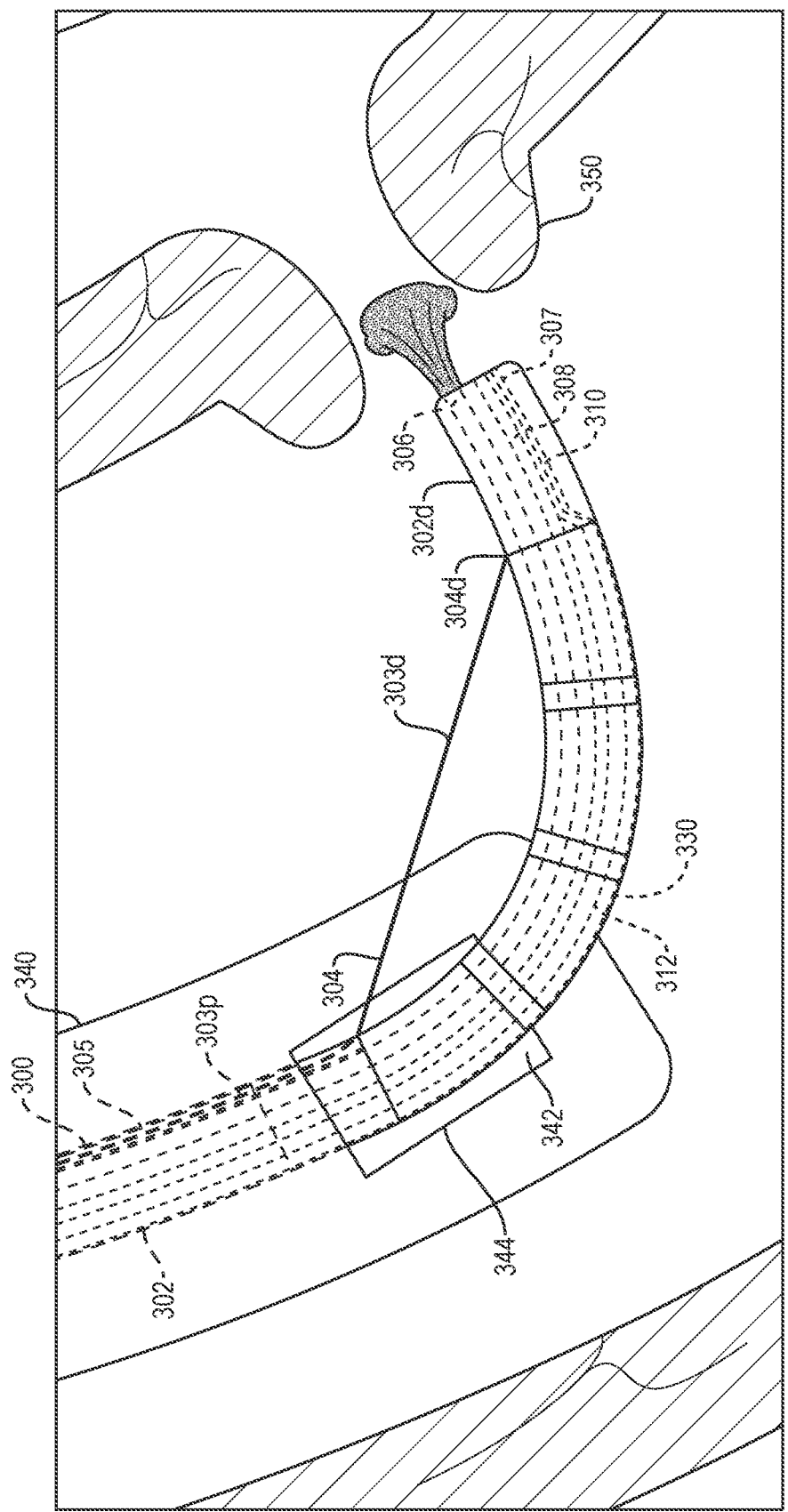
FIG. 3 illustrates a system for accessing a body lumen within a patient, according to an embodiment of the present disclosure.

With reference to FIG. 3, an embodiment of a system for accessing a body lumen according to the present disclosure is illustrated, which includes a medical device 300 (which may incorporate the configuration of the device 200 of FIG. 2A, and any of the cross-sections of FIGS. 2B-2C, 2D-2E, 2F-2G, 2H-2I, or any other number and configuration of lumens in accordance with the present disclosure) extended through an axial opening of a working channel 342 of an endoscope 340. The medical device 300 includes a flexible elongate tube 302 with a distal end $302_d$ extending out of the working channel 342 through a radial opening 344 of the endoscope 340. A wire filament 304 having a proximal end, a proximal portion $303_p$, a distal portion $303_d$, and a distal end $304_d$, extends along a portion of the elongate tube 302. The distal end $304_d$ of the filament 304 is connected to the distal end $302_d$ of the elongate tube 302. The proximal portion $303_p$ extends within the elongate tube 302 within a fourth lumen 305. The distal portion $303_d$ of the filament 304 extends external to the elongate tube 302, and assumes a bowed configuration as shown when the elongate tube 302 is bent. The distal portion $303_d$ of the filament may extend adjacently along the outer surface of elongate tube 302 or within a channel of the elongate tube 302 when the tube 302 is substantially straight. The wire filament 304 may be manipulated by a user as shown such that it directs the distal end $302_d$ of the elongate tube 302 toward the opening of the body lumen 350. A first lumen 306 extends from a proximal end of the elongate tube 302 to the distal end $302_d$. The first lumen 306 includes a fluid connection for a fluid source. With the distal end $302_d$ of the elongate tube 302 directed toward the opening of the body lumen 350, a fluid may be delivered through the first lumen 306 and towards the body lumen 350, at least partially opening or dilating the body lumen 350. A C-shaped channel 312 extends along the elongate tube 302 and removably holds a guidewire 330. The C-shaped channel 312 is in communication with a second lumen 310 at the distal end $302_d$ of the elongate tube 302. A third lumen 308 extends along the elongate tube 302 to the distal end $302_d$. The third lumen 308 and second lumen 310 may transition to a bifurcated lumen which includes a partition wall separating the bifurcated lumen into two half-lumens, e.g., to accept each of the contrast agent and the guidewire 330. In some embodiments, consistent with the above description, the fluid source and contrast source may share the same lumen, or the guidewire and contrast source may share the same lumen, or the guidewire and contrast source may remain as independent lumens, rather than having a bifurcated lumen. One or more seals at an end aperture, a side aperture (e.g., a side port), and/or along a portion of the lumen may be used to separately extend one or more devices (e.g., a guidewire) and/or supply a fluid to the lumen. If the fluid and the contrast share the same lumen, the fluid may be flowed first and the contrast may be flowed second. A fluid may be difficult to flow through a shared lumen following a flowed contrast.

Figure 4:
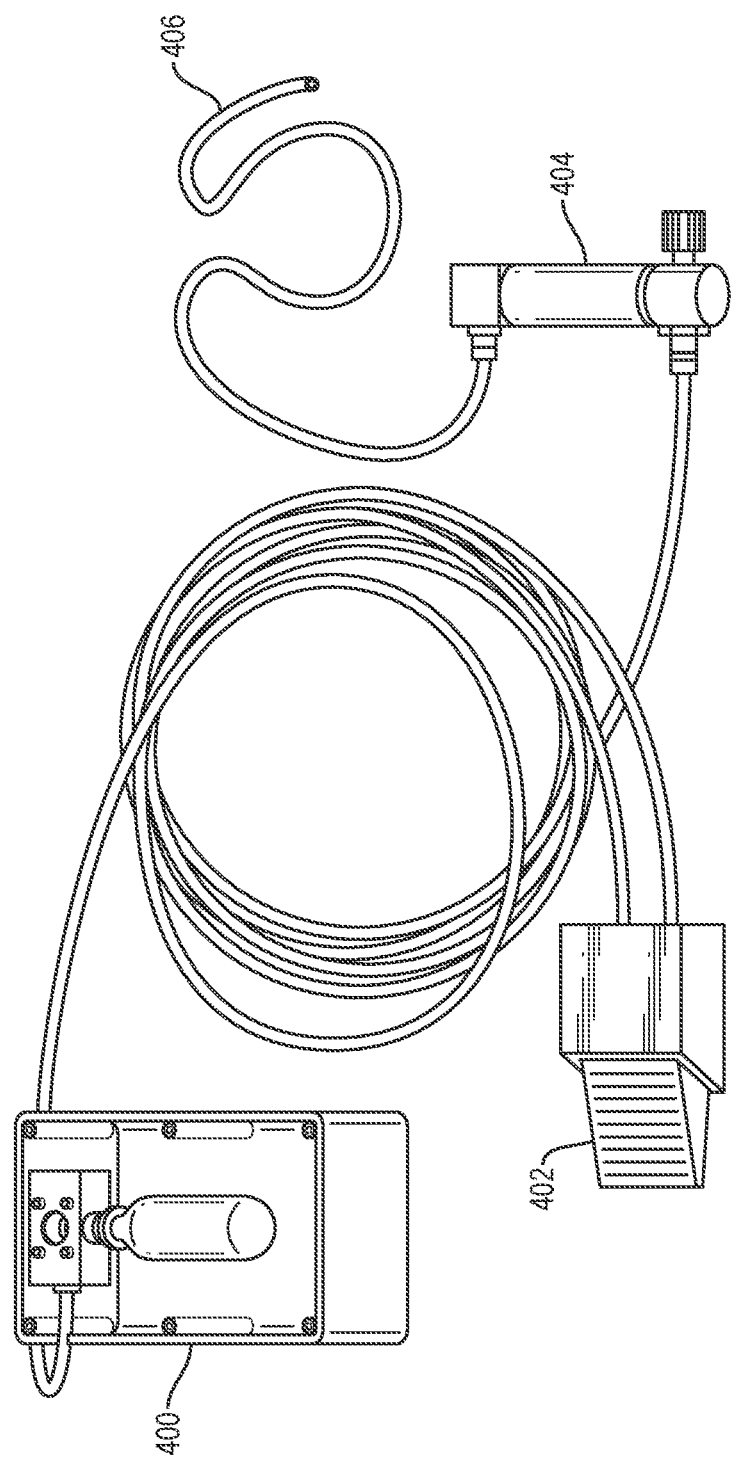
FIG. 4 illustrates components for supplying fluid within a system for accessing a body lumen, according to an embodiment of the present disclosure.

With reference to FIG. 4, an embodiment of a system for accessing a body lumen according to the present disclosure is illustrated, which includes a fluid source 400, which may be a $CO_2$ cannister within a housing that may be mounted on a mobile device such as a cart or may be fixated to a wall in an operating room. Rather than a housing with a tank, the fluid source may be a supply tube in a therapy room, a movable or immovable tank of fluid, a disposable cartridge, or a combination thereof. The fluid may be non-hazardous gas such as $CO_2$, nitrous oxide, air, inert gasses, a saline, any biocompatible fluid, or the like. The fluid may include a pharmacological agent such as a muscle relaxer. The fluid source 400 may be connected to a flow regulator 402, which may be a foot petal for a user to regulate the flow of the fluid from the fluid source 400 to a medical device. A flowmeter 404 may be in line with the flow of fluid from the source 400 to the medical device to measure the flow of fluid to a fluid connection 406 to the medical device. A flow rate of the flowmeter 404 may be monitored such that the flow rate of the fluid out of the distal end of a device is, e.g., about 400 cc/m to about 1480 cc/m, about 400 cc/m to about 800 cc/m, about 0 cc/m to about 1000 cc/m, or the like. An outlet pressure of a fluid source may be about 5 psi to about 30 psi, 6 psi to about 18 psi, or any unit of pressure within these ranges. The fluid source arrangement described for FIG. 4 could be used in any of the foregoing or other embodiments of the present disclosure.

Figure 5:
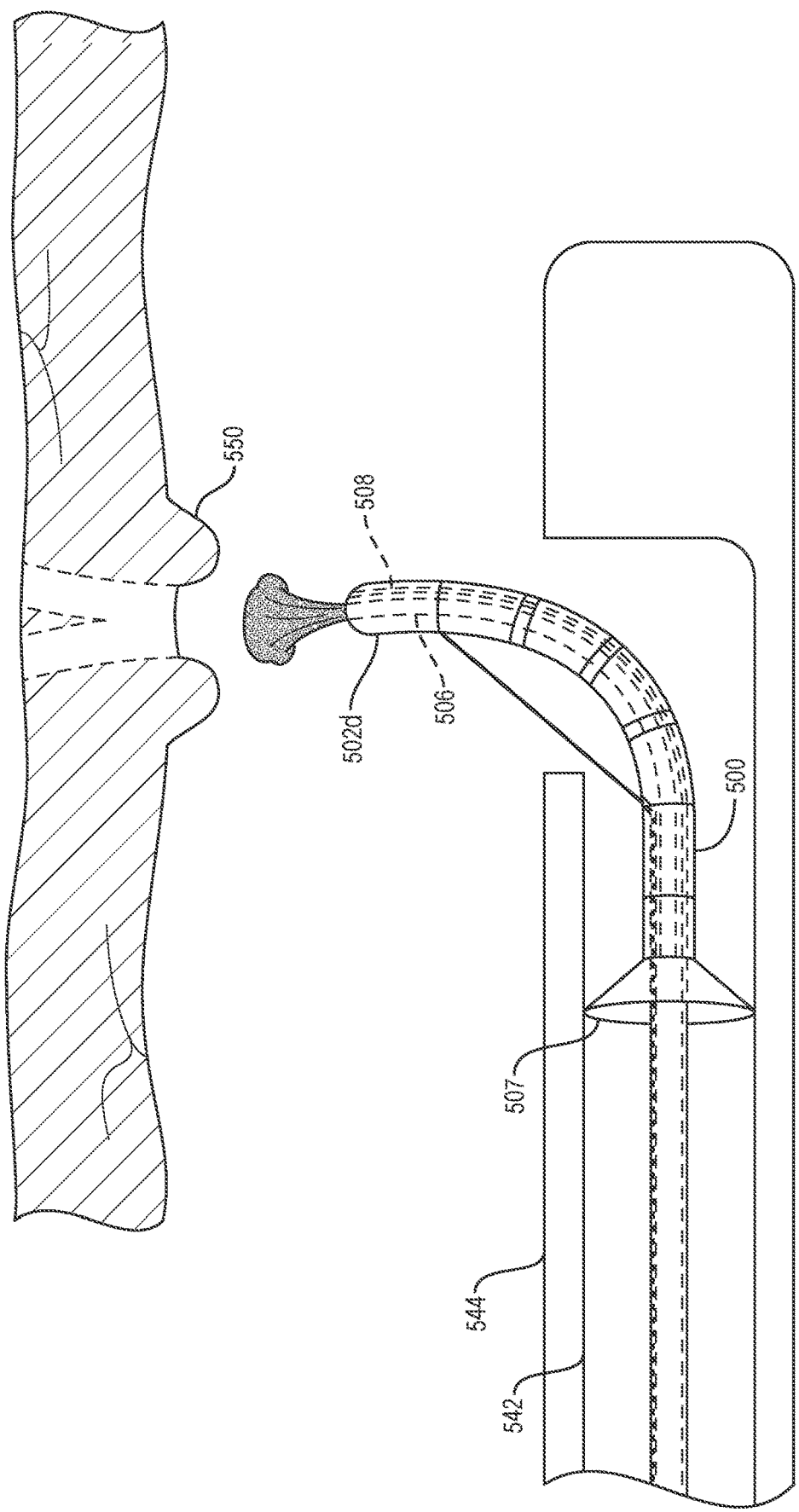
FIG. 5 illustrates a system for accessing a body lumen, according to an embodiment of the present disclosure.

With reference to FIG. 5, an embodiment of a system for accessing a body lumen according to the present disclosure is illustrated, wherein a first lumen 506 extends through a distal end $502_d$ of the elongate tube. The first lumen 506 extends from the distal end of the tube at least partially along the tube proximally and terminates at a radial skirt 507 of the elongate tube 502. The radial skirt 507 is about the elongate tube 502, and has a funnel shape tapering inward toward the direction of the distal end $502_d$ of the tube 502. The skirt 507 is in fluid communication with an opening to the first lumen 506. The skirt 507 has an outer diameter that is configured to be in substantial contact with an inner diameter of a working channel 542 of an endoscope 544. Fluid may be delivered from a fluid source into the working channel 542, into the funnel shape of the skirt 507, through the opening into the first lumen 506, and out of the first lumen 506 at the distal end $502_d$ of the elongate tube 502 toward the body lumen 550. Other lumens, such as those described above, may be included through the elongate tube 502 such as a bifurcated lumen 508 with a partition wall that creates two half-lumens, each of which, e.g., are configured to accept a guidewire and a contrast agent. The skirt may comprise one or more plastics such as polyethylene, polyurethane, pebax, and the like.

The devices, systems, and methods of the present disclosure may be used as sphincterotomes for cannulation, papillotomy, sphincterotomy, and the like. Exemplary devices, systems, and methods with which embodiments of the present disclosure may be implemented include, but are not limited to, those described in U.S. Pat. Nos. 6,676,659, 6,827,718, 7,371,237, 7,635,363, 8,231,621, 8,579,895, and 9,352,124, and U.S. patent application Ser. No. 15/158,052, each of which are herein incorporated by reference in their entirety. Exemplary devices described therein may be modified to incorporate embodiments or features of the present disclosure. Alternatively, various embodiments of devices, systems, and methods of the present disclosure may not include features of the above-identified properties. For example, a medical device may not include a wire filament, a guide wire, a contrast agent, and/or lumens other than a lumen in fluid communication with a fluid source to deliver the fluid for purposes of accessing a body lumen substantially without or without contacting the opening of the body lumen.

In various embodiments, described here or otherwise within the scope of the present disclosure, a lumen of the flexible elongate tube may be configured to receive a guidewire such that a distal portion of the guidewire may extend distally beyond the distal end of the elongate tube. The elongate tube may include a flexible distal portion configured to move (e.g., flex, bend, rotate, wobble, spin, etc.) in a plurality of directions (e.g., x, y and/or z directions), thereby imparting an identical or similar direction of movement to the distal portion of the guidewire. The distal portion of the elongate tube may be configured to move in a linear motion (e.g., moving in a single direction along a straight line relative to a longitudinal axis of the elongate tube), or in a reciprocating motion (e.g., backwards and forwards in a straight line along a longitudinal axis of the elongate tube). The distal portion of the elongate tube may be configured to swing from side-to-side in a vibrating or oscillatory motion. The distal portion of the elongate tube may be configured to move in a rotary motion (e.g., 360 degrees of rotation around a central axis of the elongate member).

In various embodiments, described here or otherwise within the scope of the present disclosure, a wire filament may be a cutting wire extending through or along a length of the elongate tube. A distal end of the filament may be attached to the elongate tube at or near the distal end, and a proximal end of the filament may be attached to an energy source. A portion of the filament that is coextensive with a distal portion of the elongate tube may be unattached and configured to extend at an outward angle relative to a longitudinal axis of the elongate tube as the distal portion bends or flexes. With the distal portion of the elongate tube held in a bent or flexed position, the medical professional may activate the energy source to energize the angled portion of the filament, thereby providing cutting and/or cauterizing energy that may, e.g., enlarge or further enlarge an opening of the target body lumen. In various embodiments, the distal portion of the elongate tube and/or the distal end of the filament may be configured to deliver real-time feedback information to a medical professional or computer processor, to manually or automatically adjust, e.g., increase or decrease, the frequency, power, and/or duration of energy being delivered.

In various embodiments, described here or otherwise within the scope of the present disclosure, fluoroscopy may assist in positioning a system or medical device, or for confirming the location of lumens, tissues, ducts, presence of one or more bodies such as gallstones, etc. A contrast agent may be injected through a medical device and into or about the body lumen for fluoroscopy. A contrast agent may be injected through a lumen of the medical device. A guidewire may be withdrawn from a lumen to allow the contrast agent to be injected through the lumen. Alternatively, a contrast agent may be injected in a lumen containing a guidewire such that the contrast agent flows through the lumen about the guidewire. Alternatively, a lumen or a portion of a multi-lumen (e.g., a bifurcated lumen) may be dedicated to the flow of a contrast agent and may be used to deliver contrast agent out of a medical device. Alternatively, a first lumen, e.g., a lumen in fluid communication with a fluid, may be used to open or move tissue associated with a body lumen and later be used to flow a contrast agent. Alternatively, the contrast agent may be the fluid used to manipulate the opening of the body lumen. The contrast agent may comprise iodine, barium sulfate, gadolinium, or the like, or some combination thereof. Alternatively, the contrast agent and a fluid such as a saline may be mixed together to perform both functions of providing contrast agent and opening of the body lumen.

In various embodiments, described here or otherwise within the scope of the present disclosure, a C-shaped channel may comprise other shapes such as, e.g., U-shaped, V-shaped, triangular, boxed, a combination of these shapes, etc. A channel, such as these channels may be an open channel or a closed channel. A closed channel may have one or more portions of varying wall thickness, e.g., a thinner wall at a portion of the channel configured for a user to remove an object (e.g., a guidewire) from the channel by pulling or tearing the guidewire through the thinner portion of the wall. A wall of a closed channel may be perforated, e.g., for easier removal of the guidewire.

In various of the embodiments, described here or otherwise within the scope of the present disclosure, a bifurcated lumen may include a partition wall along at least a portion of a bifurcated lumen that separates the lumen into two half-lumens. Each of the two half-lumens may not be in fluid communication with each other such that each one may accept different fluids or objects, e.g., a contrast agent and a guidewire. The proximal portion of the bifurcated lumen may transition to two independent lumens. In embodiments, a lumen may be divided into more than two half-lumens, e.g., three, four, or more lumens, which that may be equal in dimension or have different dimensions. The partition wall may be destructible such that, e.g., a distal portion of the partition wall may be destroyed or removed such that the parts of the bifurcated lumen converge together into one lumen. The length of the partition wall that is destroyed or removed may be customizable by the user. For example, the partition wall may be at least partially destructible at the distal end of a tube. Converged lumens may allow for a smaller diameter lumen extending through the distal end of the elongate tube compared to the larger diameters of the two separate lumens or half-lumens, allowing in some cases for more space at the distal end for other of the lumens. The separate half-lumens or lumens extending throughout most of the elongate tube may allow for multiple fluids to travel independently along most of the length of tube and exit the distal end of the elongate tube, without the multiple fluids pressing against each other along the length (as may be the case with fluids sharing a lumen along most of the length of the tube).

In various embodiments, described here or otherwise within the scope of the present disclosure, a lumen of a medical device for the flow of a fluid may include a nozzle at the distal end of the lumen. The nozzle may be the same diameter as the remainder of the lumen or smaller than the remainder of the lumen. A smaller diameter nozzle may increase the flow rate and/or pressure of the fluid at the exit point of the lumen and may allow for a more targeted or concentrated flow of the fluid to the body lumen and associate tissue. The nozzle may have a cross-section normal to a longitudinal axis of the lumen that is a different shape than the remainder of the lumen such as a rectangle, square, ellipsoid, any combination of these shapes, or the like.

In various embodiments, described here or otherwise within the scope of the present disclosure, a user may direct a distal end of a tube and lumen for supplying a fluid toward an opening of a body lumen. The lumen may or may not be axially aligned with the opening. The distal end of the lumen may be positioned substantially axially with the opening of the papilla and may be positioned at a discretion of the user, e.g., about 5 millimeters to about 10 millimeters, away from the opening of the body lumen before and or during delivery of the fluid towards the body lumen. Fluid may be delivered throughout the cannulation procedure and the fluid delivery may be ceased after cannulation. The delivery of fluid may work to mechanically open the papilla with the fluid being flowed at some pressure against or through the papilla. Delivering fluid during cannulation or after into the biliary tree itself may be acceptable in some circumstances, with the understanding that an over-pressure or over-volume in the biliary tree may present complications.

In various embodiments, methods of accessing a body lumen may include extending an endoscope having a working channel into a patient. An elongate tube having a distal end and a lumen may be extended through the working channel. The distal end of the tube may be directed toward an opening of the body lumen. A fluid may be flowed from a fluid source through the lumen to the distal end of the tube. The fluid may be delivered to the opening of the body lumen and may dilate the opening of the body lumen. A guidewire may be extended through the tube into the body lumen. The tube may be removed from about the guidewire and may be removed from the working channel such that the guidewire may be left within the working channel and within the body lumen. Another instrument may be inserted within the working channel over the guidewire and into the body lumen. A contrast agent may be flowed into the body lumen. A flow rate of the fluid flowing through the tube may be adjusted. Adjustment of the flow rate may assist with opening/dilating the body lumen. The flow rate may be adjusted such that no contact is made with the body lumen and surrounding tissue. Directing the distal end of the tube may comprise aligning the tube substantially axially with the opening of the body lumen. The distal end may be aligned at a distance of about 5 millimeters to about 10 millimeters away from the opening of the body lumen. The endoscope may be extended through the stomach and into the duodenum of the patient. The body lumen may be a papilla.

The medical devices of the present disclosure are not limited to duodenoscopes, and may include a variety of medical devices for accessing body passageways, including, for example, catheters, ureteroscopes, bronchoscopes, colonoscopes, arthroscopes, cystoscopes, hysteroscopes, and the like.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
a flexible elongate tube having a proximal end and a distal end configured to be directed toward an opening of a body lumen;
a first lumen extending from a distal-most end of the tube at least partially along the tube toward the proximal end of the tube, the first lumen having a fluid connection at a proximal end for a fluid source;
a second lumen extending from the distal-most end of the tube at least partially along the tube toward the proximal end of the tube, the second lumen configured to accept a guidewire extending along the second lumen;
a wire filament extending along the elongate tube, a distal end of the filament connected to the distal end of the elongate tube, a proximal portion of the wire extending at least partially along the elongate tube, and a distal portion of the wire extending external to the elongate tube; and
a radial skirt about the elongate tube, the skirt having a funnel shape tapering inward toward the distal end of the tube, wherein a distal end of the skirt is in fluid communication with an opening to a proximal end of the first lumen, and wherein the skirt has an outer diameter configured to be in substantial contact with an inner diameter of a working channel of an endoscope, such that fluid may be delivered from a fluid source into the working channel, into a proximal end of the skirt, through the opening to the proximal end of the first lumen, into the first lumen, and out of the first lumen at the distal-most end of the first lumen.

2. The medical device of claim 1, further comprising a third lumen extending along the tube and configured to deliver a contrast agent.

3. The medical device of claim 2, further comprising a bifurcated lumen at the distal-most end of the tube that includes a partition wall separating the bifurcated lumen into two half-lumens.

4. The medical device of claim 3, wherein the second lumen transitions to and terminates at a distal-most end of one of the two half-lumens and the third lumen transitions to the other of the two half-lumens.

5. The medical device of claim 1, wherein the first lumen is configured to deliver a gas as the fluid source from the first lumen at the distal end of the tube to at least partially open the body lumen for access substantially without the medical device contacting the body lumen.

6. The medical device of claim 1, further comprising a channel extending at least partially along an outer surface of the elongate tube and transitioning to the second lumen.

7. The medical device of claim 1, further comprising a fourth lumen extending along the tube and a handle at the proximal end of the tube and connected to the proximal end of the wire filament, wherein the proximal portion of the wire is slidably extending within the fourth lumen, and wherein the handle is configured to slide the wire filament within the fourth lumen such that the distal end of the tube is directed toward the opening of the body lumen.

8. A medical device, comprising:
  a flexible elongate tube having a proximal end and a distal end configured to be directed toward an opening of a body lumen;
  a first lumen extending from the distal end of the tube at least partially along the tube toward the proximal end of the tube, the first lumen opening to an exterior of the device at a distal end of the first lumen and having a fluid connection at a proximal end for a fluid source;
  a second lumen extending from the distal end of the tube at least partially along the tube toward the proximal end of the tube, the second lumen configured to accept a guidewire extending along the second lumen, and the second lumen opening to an exterior of the device at a distal end of the second lumen;
  a wire filament extending along the elongate tube, a distal end of the filament connected to the distal end of the elongate tube, a proximal portion of the wire extending at least partially along the elongate tube, and a distal portion of the wire extending external to the elongate tube; and
  a radial skirt about the elongate tube, the skirt having a funnel shape tapering inward toward the distal end of the tube, wherein a distal end of the skirt is in fluid communication with an opening to a proximal end of the first lumen, and wherein the skirt has an outer diameter configured to be in substantial contact with an inner diameter of a working channel of an endoscope, such that fluid may be delivered from a fluid source into the working channel, into a proximal end of the skirt, through the opening to the proximal end of the first lumen, into the first lumen, and out of the first lumen at the distal end of the first lumen.

9. The medical device of claim 8, further comprising a third lumen extending along the tube and configured to deliver a contrast agent.

10. The medical device of claim 9, further comprising a bifurcated lumen at a distal-most end of the tube that includes a partition wall separating the bifurcated lumen into two half-lumens.

11. The medical device of claim 10, wherein the second lumen transitions to one of the two half-lumens and the third lumen transitions to the other of the two half-lumens.

12. The medical device of claim 8, wherein the first lumen is configured to deliver a gas as the fluid source from the first lumen at the distal end of the tube to at least partially open the body lumen for access substantially without the medical device contacting the body lumen.

13. The medical device of claim 8, further comprising a fourth lumen extending along the tube and a handle at the proximal end of the tube and connected to the proximal end of the wire filament, wherein the proximal portion of the wire is slidably extending within the fourth lumen, and wherein the handle is configured to slide the wire filament within the fourth lumen such that the distal end of the tube is directed toward the opening of the body lumen.

14. A medical device, comprising:
  a flexible elongate tube having a proximal end and a distal end configured to be directed toward an opening of a body lumen;
  a first lumen extending from the distal end of the tube at least partially along the tube toward the proximal end of the tube, the first lumen having a fluid connection at a proximal end for a fluid source;
  a second lumen extending from the distal end of the tube at least partially along the tube toward the proximal end of the tube, the second lumen configured to accept a guidewire extending along the second lumen;
  a wire filament extending along the elongate tube, a distal end of the filament connected to the distal end of the elongate tube, a proximal portion of the wire extending at least partially along the elongate tube, and a distal portion of the wire extending external to the elongate tube;
  a C-shaped channel extending at least partially along an outer surface of the elongate tube, the C-shaped channel transitioning to the second lumen; and
  a radial skirt about the elongate tube, the skirt having a funnel shape tapering inward toward the distal end of the tube, wherein a distal end of the skirt is in fluid communication with an opening to a proximal end of the first lumen, and wherein the skirt has an outer diameter configured to be in substantial contact with an inner diameter of a working channel of an endoscope, such that fluid may be delivered from a fluid source into the working channel, into a proximal end of the skirt, through the opening to the proximal end of the first lumen, into the first lumen, and out of the first lumen at the distal end of the first lumen.

15. The medical device of claim 14, further comprising a third lumen extending along the tube and configured to deliver a contrast agent.

16. The medical device of claim 14, wherein the first lumen is configured to deliver a gas as the fluid source from the first lumen at the distal end of the tube to at least partially open the body lumen for access substantially without the medical device contacting the body lumen.

17. The medical device of claim 14, further comprising a fourth lumen extending along the tube and a handle at the proximal end of the tube and connected to the proximal end of the wire filament, wherein the proximal portion of the wire is slidably extending within the fourth lumen, and wherein the handle is configured to slide the wire filament within the fourth lumen such that the distal end of the tube is directed toward the opening of the body lumen.

* * * * *